US005430156A

United States Patent [19]

Arnost et al.

[11] Patent Number: 5,430,156

[45] Date of Patent: Jul. 4, 1995

[54] COLOR-PROVIDING COMPOUND HAVING TWO OR MORE CYCLIC 1,3 SULFUR-NITROGEN GROUPS AND TWO OR MORE COLOR-PROVIDING MOIETIES

[75] Inventors: Michael J. Arnost, Andover; Efthimios Chinoporos, Cambridge; Donald A. McGowan, Bedford; David P. Waller, Lexington, all of Mass.

[73] Assignee: Polaroid Corporation, Cambridge, Mass.

[21] Appl. No.: 191,084

[22] Filed: Feb. 4, 1994

Related U.S. Application Data

[62] Division of Ser. No. 923,843, Jul. 31, 1992, Pat. No. 5,316,887.

[51] Int. Cl.$^6$ .......... C07D 417/12

[52] U.S. Cl. .......... 548/146; 544/54

[58] Field of Search .......... 548/146; 544/54

[56] References Cited

U.S. PATENT DOCUMENTS

| | | | |
|---|---|---|---|
| 3,719,489 | 3/1973 | Cieciuch et al. | 96/29 |
| 4,098,783 | 7/1978 | Cieciuch et al. | 260/147 |
| 4,468,448 | 8/1984 | Rogers | 430/222 |

FOREIGN PATENT DOCUMENTS

| | | |
|---|---|---|
| 0082506 | 6/1983 | European Pat. Off. . |
| 0173404 | 3/1986 | European Pat. Off. . |
| 0345839 | 12/1989 | European Pat. Off. . |
| 59-180548 | 10/1984 | Japan . |

OTHER PUBLICATIONS

Felder, et al., Chemical Abstracts, vol. 55, No. 4, 3423 c–h, (1961).

*Primary Examiner*—Robert Gerstl
*Attorney, Agent, or Firm*—Edward W. Black

[57] ABSTRACT

There are disclosed color-providing compounds comprising two or more cyclic 1,3 sulfur-nitrogen groups and two or more color-providing moieties, i.e., complete dyes or dye intermediates, capable of releasing the color-forming moieties upon cleavage in the presence of silver ions or a soluble silver complex. The color-providing compounds are useful as image-forming materials in color photographic processes.

7 Claims, No Drawings

COLOR-PROVIDING COMPOUND HAVING TWO OR MORE CYCLIC 1,3 SULFUR-NITROGEN GROUPS AND TWO OR MORE COLOR-PROVIDING MOIETIES

RELATED APPLICATIONS

This application is a divisional of copending U.S. patent application Ser. No. 07/923,843 filed Jul. 31, 1992 (now issued U.S. Pat. No. 5,316,887).

BACKGROUND OF THE INVENTION

1. Field of the Invention

This invention relates to image-forming materials, specifically to color-providing compounds which, in the presence of silver ions and/or a soluble silver complex, undergo a cleavage reaction to liberate two or more color-providing moieties.

2. Description of the Related Art

U.S. Pat. No. 3,719,489 discloses silver ion assisted cleavage reactions useful in photographic systems. As disclosed therein, photographically inert compounds are capable of undergoing cleavage in the presence of silver ions made available imagewise during processing of a silver halide emulsion to liberate a reagent, such as, a photographically active reagent or a dye in an imagewise distribution corresponding to that of said silver ions. In one embodiment disclosed therein, color images are produced by using as the photographically inert compounds, color providing compounds which are substantially non-diffusible in the photographic processing composition but capable of undergoing cleavage in the presence of the imagewise distribution of silver ions and/or soluble silver complex made available in the undeveloped and partially developed areas of a silver halide emulsion as a function of development-to liberate a more mobile and diffusible color-providing moiety in an imagewise distribution corresponding to the imagewise distribution of said ions and/or said complex. The subsequent formation of a color image is the result of the differential in diffusibility between the parent compound and liberated color-providing moiety whereby the imagewise distribution of the more diffusible color-providing moiety released in the undeveloped and partially developed areas is free to transfer.

Color-providing compounds useful in the above process form the subject matter of U.S. Pat. No. 4,098,783, a continuation in part of said U.S. Pat. No. 3,719,489. The color-providing compounds disclosed therein may comprise one or more dye radicals and one or more 1,3-sulfur-nitrogen moieties. For example, they may comprise one complete dye or dye intermediate and one cyclic 1,3-sulfur-nitrogen moiety. Alternatively, the color-providing compounds may comprise two or more cyclic moieties for each dye radical or dye intermediate and vice versa. Particularly useful dye-providing compounds disclosed therein comprise a dye containing from 1 to 4 and preferably 1 or 2 cyclic 1,3-sulfur-nitrogen groups and may be represented by the formula $$D-[(L)_{m-1}-Y]_n \qquad (A)$$

wherein D represents a dye radical, i.e., the radical of an organic dye possessing at least one carbon atom, L is a divalent organic linking group containing at least one carbon atom, m is a positive integer 1 or 2, n is a positive integer from 1 to 4, and Y is a cyclic 1,3-sulfur-nitrogen group.

U.S. Pat. No. 4,468,448 discloses a different class of 1,3-sulfur-nitrogen compounds which, rather than relying on the differential in diffusibility between the colored parent compound and the liberated dye to form the color image, as in the aforementioned U.S. Pat. No. 3,719,489, utilize the ability of 1,3-sulfur-nitrogen compounds to undergo silver ion assisted cleavage to provide an imagewise distribution of a colored image dye from a substantially colorless precursor of a preformed image dye. This is accomplished by employing a 1,3-sulfur-nitrogen group to maintain said precursor in its substantially colorless form until said 1,3-sulfur-nitrogen group undergoes cleavage. The color image may be formed by using the imagewise cleavage of the 1,3-sulfur-nitrogen group to provide the image dye directly, or the imagewise cleavage of the 1,3-sulfur-nitrogen group may be used to activate a subsequent reaction or series of reactions which in turn provide the image dye.

Thermally developable black and white as well as color photosensitive materials, whose development is effected by heating, are well known. Among the systems designed to give color images are those wherein a diffusible dye is released as a result of the heat development of an organic silver salt and transferred to the image-receiving layer, whereby a color image is obtained.

Japanese Kokai 59-180548 having a Laid-Open date of Oct. 13, 1984 discloses a heat-developable silver halide photosensitive imaging system wherein the dye-providing material contains a heterocyclic ring containing a nitrogen atom and a sulfur or selenium atom which heterocyclic ring is subject to cleavage in the presence of silver ions to release a diffusible dye. An example of a suitable dye-providing material is a thiazolidine dye such as disclosed in the aforementioned U.S. Pat. No. 4,098,783. The process involves imagewise exposing the photosensitive system to light and subsequently or simultaneously heating the photosensitive system under a substantially water-free condition, in the presence of a base or base precursor, whereby an oxidation-reduction reaction between the exposed photosensitive silver halide and a reducing agent occurs. In the exposed areas a negative silver image is formed. In the unexposed areas, the silver ion, present in inverse proportion to the silver image, causes the heterocyclic ring of the dye-providing material to be cleaved releasing a diffusible dye. The diffusible dye is then transferred to an image-receiving layer whereby a positive dye image is formed.

While the differential in diffusibility between the parent compound and the liberated color-providing moiety, disclosed in the aforementioned U.S. Pat. No. 3,719,489, is useful in obtaining a color image, under some conditions a small amount of the parent compound may also transfer. Thus, in color diffusion transfer film products wherein the parent compound comprising a colored image dye-providing moiety is itself colored, non-imagewise diffusion during processing of even a minimal amount of the parent compound to a receptive layer of the film unit can adversely affect the quality of the image, particularly in the Dmin, i.e., highlight, areas of the image. This has been found to be a particularly acute problem in thermally developed silver halide photographic systems.

One way to lessen the diffusion of uncleaved dye-providing material is to add additional ballasting groups and/or to increase the size of the ballast groups. However, this is not very efficient since it requires a larger weight of uncleaved dye-providing material for the same amount of dye released.

It has been now been found that by using additional dye providing radicals as ballast groups, one can decrease diffusion of the uncleaved parent compound to the receptive layer of the film unit while increasing the image-forming efficiency of the color-providing materials, i.e., releasing more dye-providing moieties per molecule of uncleaved color-providing material.

SUMMARY OF THE INVENTION

According to the present invention, color-providing compounds are provided which comprise two or more cyclic 1,3-sulfur-nitrogen groups and two or more color-providing moieties. Specifically, the color-providing compounds of the present invention comprise two to four groups, the same or different, the groups being represented by the general formula Formula I

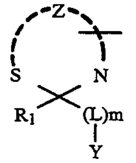

wherein Y represents a color-providing moiety; L represents a divalent organic linking group containing at least one carbon atom; m is 0 or 1; $R_1$ represents hydrogen, a monovalent organic radical or together with L represents the atoms necessary to complete a spiro union with the cyclic 1,3-sulfur-nitrogen group when m is 1 or together with Y represents the atoms necessary to complete a spiro union with the cyclic 1,3-sulfur-nitrogen group when m is 0; and Z represents the carbon atoms necessary to complete an unsubstituted or substituted 5- or 6-membered heterocyclic ring system provided each group represented by Formula I is connected to the others by a multivalent chemical linkage which connects the groups through the N atom or through the C atoms represented by Z.

The color-providing compounds of the present invention are useful in photographic imaging systems utilizing silver halide wherein the method of processing employs either wet processing to develop the image such as disclosed in the aforementioned U.S. Pat. No. 3,719,489, or dry processing which develops the image by heating. The dry processed photographic systems may be those processed in the presence of base or a base-precursor, i.e., a compound which generates a base under the processing conditions, such as those disclosed in the aforementioned Japanese Kokai No. 59-180548, or they may be those processed in the absence of base or a base precursor. In photographic systems, the compounds of this invention are capable of releasing two or more color-providing moieties, the same or different, in the presence of the imagewise distribution of silver ions or silver salt complex made available during processing of a silver halide emulsion, in an imagewise distribution corresponding to that of the silver ions. The color-providing compounds are also useful in thermographic imaging systems wherein a source of silver ions or a soluble silver complex becomes available, upon heating in an imagewise manner, to cleave the color-providing compounds. While a particular color-providing compound may be useful in one imaging system, it may not be suitable for use in another. This could be due to, among other things, differences in solubility and/or diffusibility of the color-providing compound and/or the released color-providing moiety within the various imaging systems. However, one of skill in the art will be able to modify the color-providing compounds by choice of functional groups so that they will function as desired in a particular system.

The compounds of the present invention are particularly useful in heat-developable photographic imaging systems which utilize a color-providing compound according to the present invention to release a diffusible dye in an imagewise distribution corresponding to that provided by the imagewise distribution of silver ions and/or soluble silver complex formed as a function of thermal development of an imagewise exposed photosensitive element. In photothermal systems such as these, the color-providing compounds of the present invention provide improved Dmin, i.e., reduced build-up of color-providing compound in the Dmin areas of the image, when compared with analogous systems utilizing color-providing compounds comprising one dye moiety and one or more cyclic 1,3-sulfur-nitrogen groups, such as disclosed in the aforementioned U.S. Pat. No. 4,098,783. In addition, the color-providing compounds of the present invention are more efficient, that is, they provide more color-providing moiety per unit of molecular weight than dyes containing one color-providing moiety and one or more cyclic 1,3-sulfur-nitrogen groups and having a similar ballasting potential, i.e., a similar ability to prevent the color-providing compound from migrating prior to cleavage of the 1,3-sulfur-nitrogen groups.

The present invention also provides for heat-developable photosensitive materials using the above described color-providing materials.

Other provisions of the invention will in part be obvious and will in part appear hereinafter.

The invention accordingly comprises the processes involving the several steps and relation and order of one or more of such steps with respect to each of the others, and the product and compositions possessing the features, properties and relation of elements which are exemplified in the following detailed disclosure, and the scope of the application of which will be indicated in the claims.

For a fuller understanding of the nature and objects of the invention, reference should be had to the following detailed description.

DETAILED DESCRIPTION OF THE INVENTION

The color-providing compounds of the present invention are compounds which comprise two to four groups, the same or different, the groups being represented by Formula I, above. The cyclic moiety containing the group

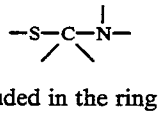

included in the ring undergoes cleavage between the S atom and the C atom common to the S and N atoms and between the N atom and the common C atom in the presence of silver ions or a soluble silver complex to release the color-providing moiety.

The term color-providing moiety is used herein to mean a complete dye or dye intermediate capable of yielding a complete dye upon subsequent reaction. The term "complete dye" is used herein to mean a dye radical comprising the chromophoric system of a dye.

One embodiment of the color-providing compounds of the present invention may be represented as shown in Formula II Formula II

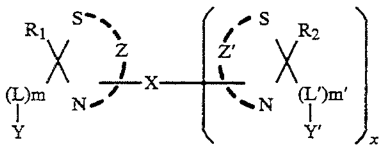

wherein Y and Y' represent color-providing moieties, the same or different; L and L' represent divalent organic linking groups, the same or different, each containing at least one carbon atom; m and m', the same or different, are 0 or 1; X represents a multivalent chemical linkage joining the cyclic 1,3-sulfur-nitrogen groups through their N atoms or the carbon atoms represented by Z and Z'; $R_1$ and $R_2$, the same or different, represent hydrogen, a monovalent organic radical or together with L or L' represent the atoms necessary to complete a spiro union with one of the cyclic 1,3-sulfur-nitrogen groups when m or m' is 1 or together with Y or Y' represents the atoms necessary to complete a spiro union with one of the cyclic 1,3-sulfur-nitrogen groups when m or m' is 0; Z and Z' the same or different, represent the atoms necessary to complete an unsubstituted or substituted 5- or 6-membered heterocyclic ring system; and x represents a positive integer from 1 to 3.

The color-providing moieties according to the present invention may be complete dyes or dye intermediates capable of yielding complete dyes upon subsequent reaction, for example, upon reaction with a suitable coupler to form a complete dye. The coupling reaction may take place directly after cleavage of the cyclic 1,3-sulfur-nitrogen group to liberate the dye intermediate, or it may take place after diffusion of the dye intermediate to, e.g., the image-receiving layer.

Complete dyes which may be used in the present invention include any of the general classes of dyes heretofore known in the art, for example, nitro, thiazole, cyanine, di- and triphenylmethane, anthrapyridone, azo, anthraquinone, phthalocyanine and metal complexed azo, azomethine and phthalocyanine dyes. Specific radicals of organic dyes that may be used include the dye radicals comprising the dye portion of the dye developers disclosed in U.S. Pat. Nos. 3,076,808; 3,076,820; 3,134,762; 3,134,763; 3,134,764; 3,134,765; 3,135,734; 3,173,906; 3,186,982; 3,201,384; 3,208,991; 3,209,016; 3,218,312; 3,236,864; 3,236,865; 3,246,016; 3,252,969; 3,253,001; 3,255,206; 3,262,924; 3,275,617; 3,282,913; 3,288,778; 3,299,041; 3,303,183; 3,306,891; 3,337,524; 3,337,589; 3,357,969; 3,365,441; 3,424,742; 3,482,972; 3,491,127; 3,544,545; 3,551,406; 3,597,200; 3,752,836; 4,264,701; and 4,267,251. Preferred dyes are the azomethine, indoaniline, indamine, and indophenol dyes, i.e., coupler dyes formed by the oxidative coupling of a phenylene diamine with a color coupler.

The dye intermediates which may be used as the color-providing moiety may comprise any molecule which when released is capable of forming a dye upon reaction with another molecule. For example, see U.S. Pat. No. 3,719,488 which discloses the use of 1,3-sulfur-nitrogen compounds to provide the imagewise distribution of dye intermediate and/or color-forming reagent, e.g., a colorless aldehyde or ketone dye intermediate which, when released is capable of reacting with a color-forming reagent, such as a methylene coupler, to form a complete dye.

In addition to the above, useful color-providing moieties include compounds which are colorless or of a color other than that ultimately desired in a certain environment, such as at a particular pH level, but upon a change in environment, e.g., from acid to alkaline conditions, take on a color change. Color-providing materials of this nature include indicator dyes and leuco dyes. It is also contemplated that dyes may be employed which undergo a color shift or change in spectral absorption characteristics during or after processing.. Such dyes may be referred to as 'temporarily shifted' dyes. The temporary shift may, for example, be effected by acylation, the acyl group being removable by hydrolysis in an alkaline environment, see for example, U.S. Pat. No. 4,535,051. The temporary shift may be effected by an amide group which undergoes an intramolecular cleavage to form a colored image dye such as disclosed in U.S. Pat. No. 4,468,451; or the temporary shift may be effected such that the colorless precursor undergoes a $\beta$-elimination reaction following the imagewise cleavage of the cyclic 1,3-sulfur-nitrogen group to form an image dye as disclosed in U.S. Pat. No. 4,468,449 or the colorless precursor undergoes a $\beta$-elimination reaction which generates a moiety capable of undergoing an intramolecular accelerated nucleophilic displacement reaction to provide an image dye as described in U.S. Pat. No. 4,468,450. It is also within the scope of the present invention to employ metal complexed or metal complexable dyes and to employ dyes, the non-complexed forms of which are substantially colorless, but which, when complexed during or subsequent to image formation, are of the desired color.

The choice of color-providing moiety is primarily limited by the spectral characteristics it is desired to have in the dye product comprising the dye radical and the cyclic 1,3-sulfur-nitrogen group.

The color-providing moieties may be linked directly to the carbon atoms of the respective 1,3-sulfur-nitrogen ring systems by a single covalent bond, an ionic bond or through a spiro union, depicted in Formula II when m=0, or they may be linked indirectly to the ring systems through appropriate linking groups, L and L' either acyclic or cyclic or a combination thereof, depicted in Formula II when m=1. The linking group, L, may be any divalent organic radical possessing at least one carbon atom for attachment to the cyclic 1,3-sulfur-nitrogen group either by a single covalent bond or by a spiro union.

Linking groups are well-known in the photographic art, and as discussed in U.S. Pat. Nos. 2,983,606 and 3,255,001, they are used to unite a dye radical of a desired predetermined color with a group possessing a silver halide developing function to obtain a dye developer. Ordinarily, the linking group functions as an insulating linkage to prevent or interrupt any system of conjugation or resonance extending from the dye radical comprising the chromophoric system of a dye to the developer group. The linking groups used in the dye developer art, either insulating or non-insulating, are also useful in the present invention for uniting the dye radical with the cyclic sulfur-nitrogen group, and divalent organic radicals appropriate for use in the present invention may be selected from those disclosed in U.S. Pat. No. 3,255,001 and those disclosed in the patents referred to above as showing useful dye radicals.

Preferably, the linking groups used in the subject color-providing compounds to connect the color-providing moieties, Y and Y' to the cyclic 1,3-sulfur-nitrogen groups comprise a divalent hydrocarbon residue, e.g., alkylene, arylene, or cycloalkylene including cycloalkyl, such as cyclohexyl; —CONH—; alkylene—CONH—; arylene—CONH—; ethylene, propylene, butylene, and phenylene. Alkylene and arylene groups have been found to be particularly useful linking groups in the present invention.

The chemical linkage, X, in Formula II, joins the cyclic 1,3-sulfur-nitrogen groups to each other. The cyclic groups may be joined through their respective nitrogen atoms or through any of their respective carbon atoms except the carbon atom common to both the N and S atoms, or the cyclic moieties may be linked through the N atom of one of the cyclic groups and a carbon atom of another, provided it is not the carbon atom common to both the S and N atoms. The chemical linkage may be a single covalent bond, as where the atoms of the respective cyclic 1,3-sulfur-nitrogen group are directly joined to each other by a shared pair of electrons, or it may be a multivalent organic group, i.e., an organic group having two, three or four free valences attached to different atoms and joined to each of the respective atoms of the 1,3-sulfur-nitrogen groups by a single covalent bond. Preferably, the chemical linkage, X, is a multivalent organic group. It is important to note that when the chemical linkage, X, joins the cyclic moieties through their respective N atoms, the chemical linkage cannot contain a carbonyl, sulfonyl or other strongly electron withdrawing group directly attached to the N atom. A strongly electron withdrawing group in that position deactivates the 1,3-sulfur-nitrogen ring so that it is not very susceptible to cleavage in the presence of silver ions and/or a soluble silver complex.

As examples of suitable chemical linkages, X, which may be used to form the color-providing compounds within the scope of the present invention, mention may be made of the following:

(a shared pair of electrons);

R—, wherein R is a bivalent hydrocarbon residue, e.g., alkylene or arylene usually containing 1 to 20 carbon atoms;

R—O—R—;

R—O—R'—, wherein R' is a bivalent hydrocarbon residue, e.g., alkylene or arylene usually containing 1 to 20 carbon atoms, different from R;

R—O—R'—O—R—;

R—O—R'—O—R''—, wherein R'' is a bivalent hydrocarbon residue, e.g., alkylene or arylene usually containing 1 to 20 carbon atoms, different from R and R';

Ar—CO—NH—R—O—R'—O—R—NH—CO—Ar—, wherein Ar represents aryl;

R—CONH—R'—NH—CO—R—

R—NH—$SO_2$—R—$SO_2$—NH—R—;

R—NH—$SO_2$—R'—$SO_2$—NH—R—;

R—NH—$SO_2$—R'—$SO_2$—NH—R''—;

NH—R—NH—R—NH—;

NH—R—NH—R'—NH—;

NH—R—NH—R—NH—R—NH—;

NH—R—NH—R'—NH—R—NH—;

N—R—NH—R'—NH—R''—NH—;

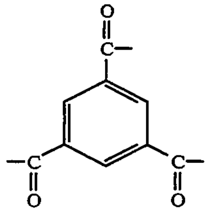

The aryl, alkylene and arylene groups referred to above are intended to also include corresponding substituted groups.

As stated above, the cyclic 1,3-sulfur-nitrogen groups are either substituted or unsubstituted 5- or 6-membered heterocyclic rings. Preferably, the cyclic groups are a thiazolidine (III) or benzothiazolidine (IV), represented by the formulae below

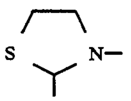

Formula III

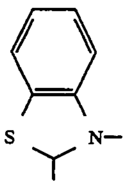

Formula IV wherein the above formulae are intended to also include the corresponding substituted thiazolidines and benzothiazolidines.

A further embodiment of the compounds of the present invention may be represented by Formula V

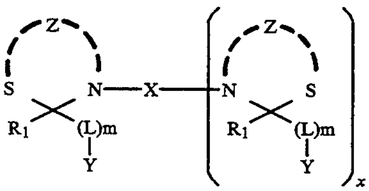

Formula V wherein $R_1$, Z, X, L, Y, m, and x all have the same meaning as above.

wherein $R_1$, Z, X, L, Y, m, and z all have the same meaning as above.

In a preferred embodiment, the compounds of the present invention may be represented by Formula VI,

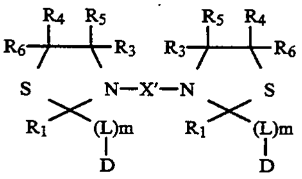

Formula VI wherein $R_1$, L and m have the same meaning as above, X' represents a bivalent organic group, $R_3$, $R_4$, $R_5$ and $R_6$ are each hydrogen, a monovalent organic radical or taken together, $R_3$ and $R_4$ or $R_5$ and $R_6$ represent a substituted or unsubstituted carbocyclic or heterocyclic ring, and D represents a complete dye, i.e., a dye radical of organic dye. Particularly useful dye radicals include those comprising the chromophoric system of an azomethine, indoaniline, indamine, and indophenol dye, e.g., a coupler dye formed by oxidative coupling of a phenylene diamine with a color coupler. Examples of coupler dyes include those described in U.S. Pat. No. 4,952,479 and J. Bailey and L. A. Williams, *The Chemistry of Synthetic Dyes,* Vol. IV, Academic Press, New York, chapter VI, 1971, pp. 341-387.

Specific examples of the color-providing compounds within the scope of the present invention are set out in the Formulae below.

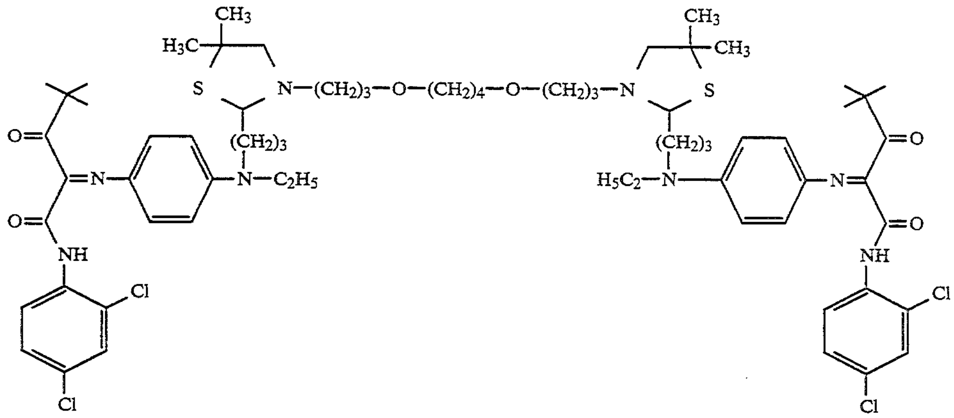

(i)

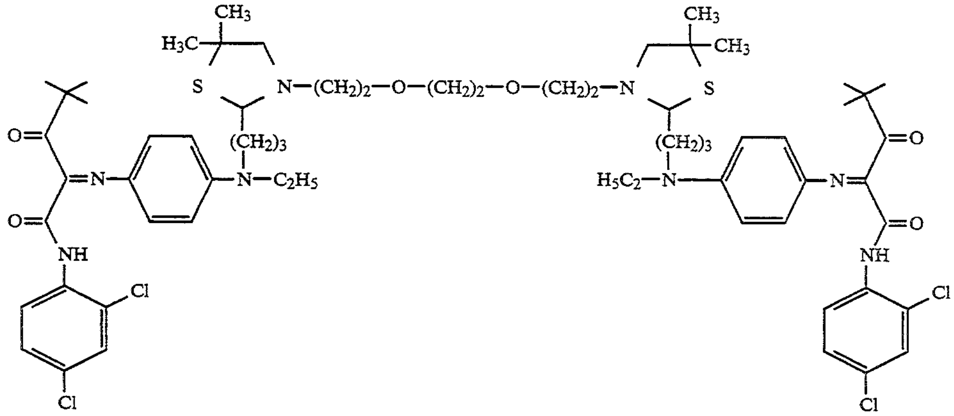

(ii)

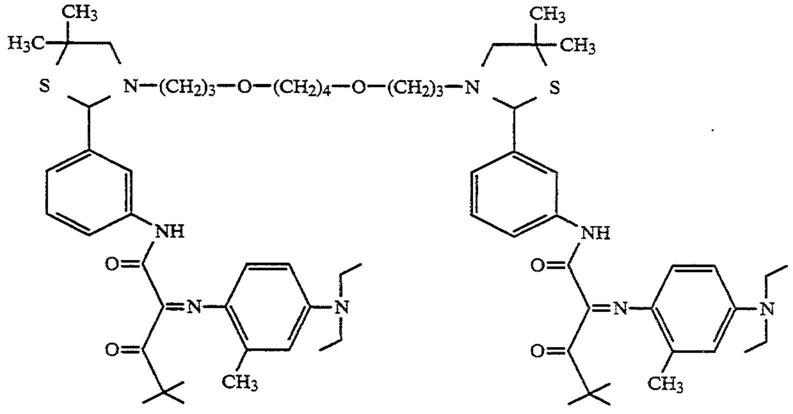

(iii)

-continued
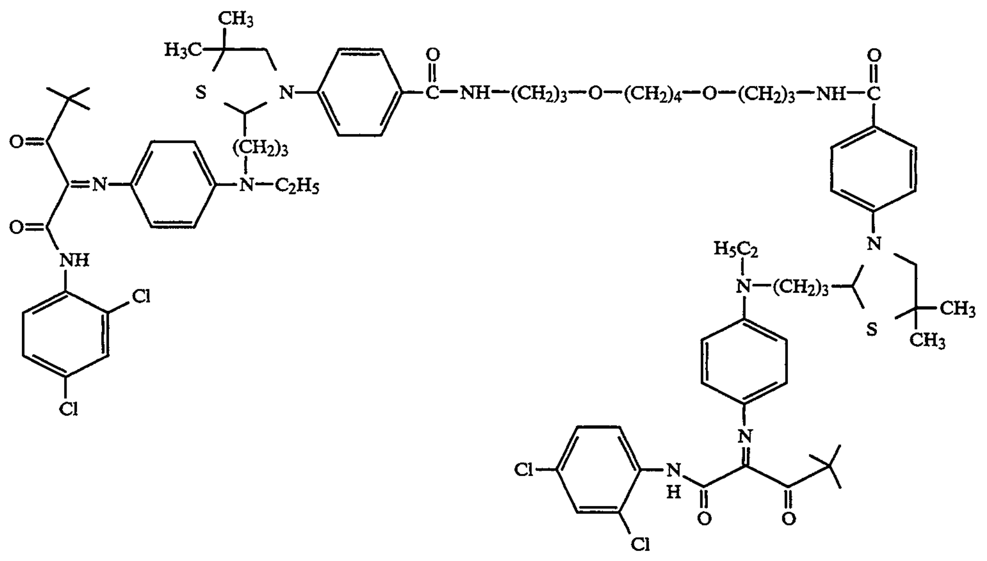
(iv)
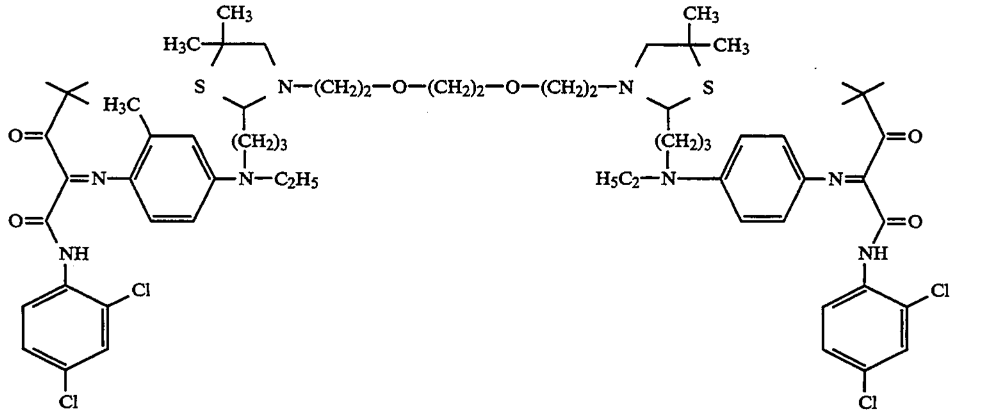
(v)
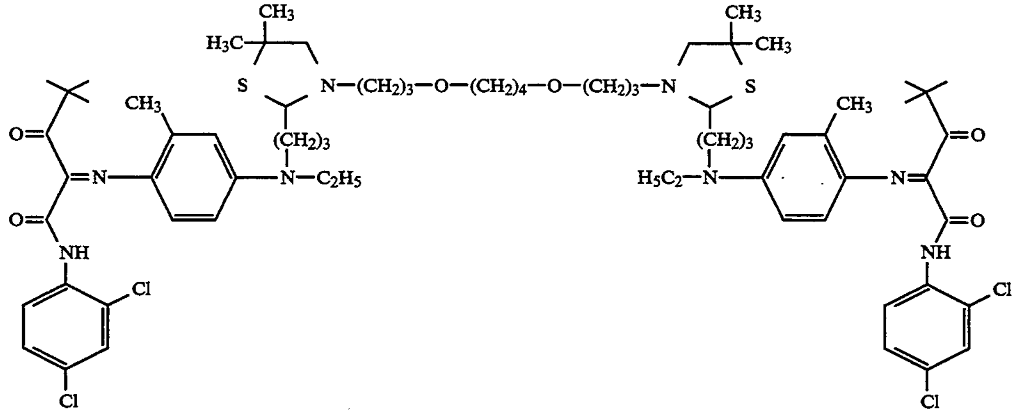
(vi)

-continued
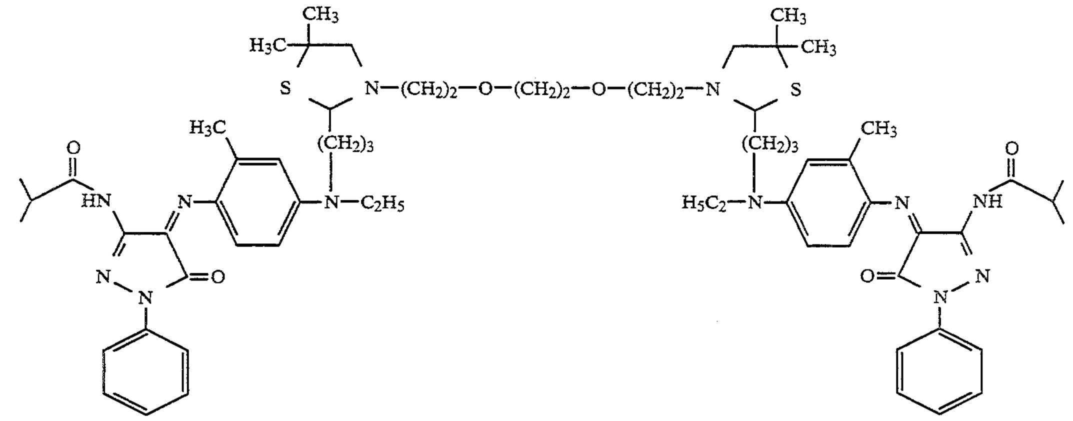
(vii)
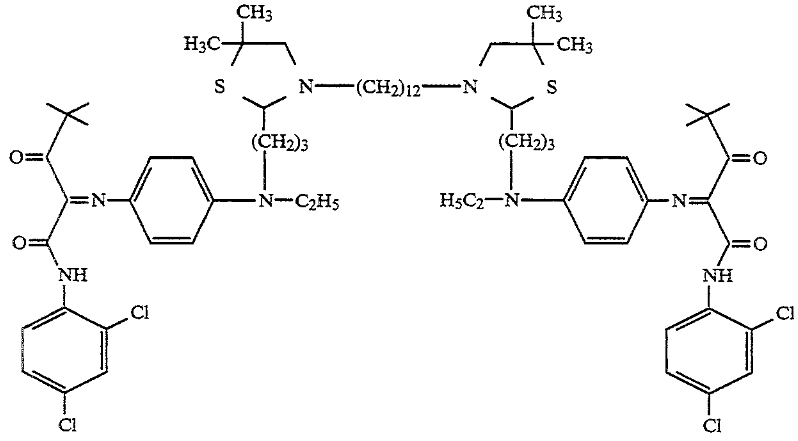
(viii)
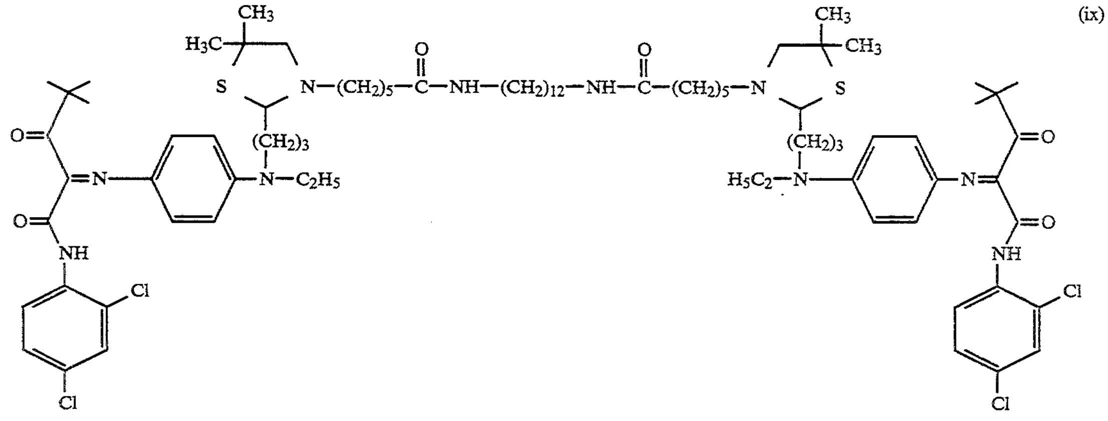
(ix)

-continued (x)

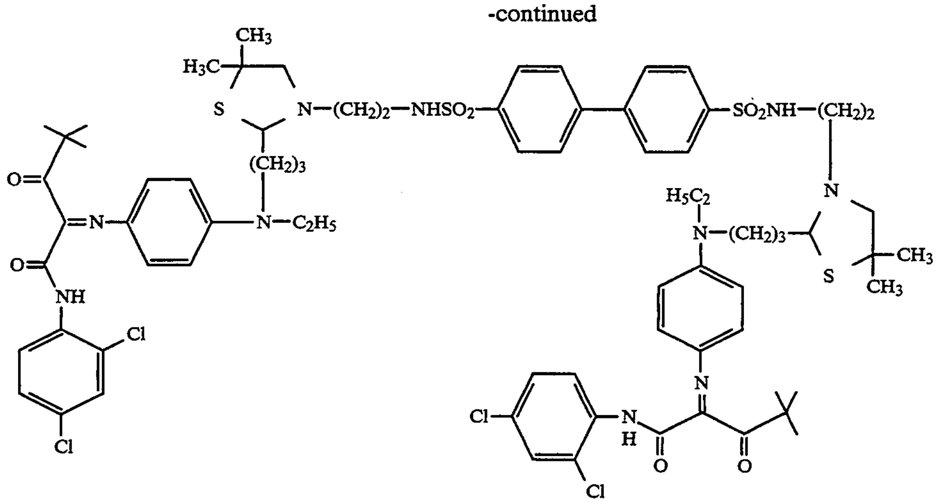

(xi)

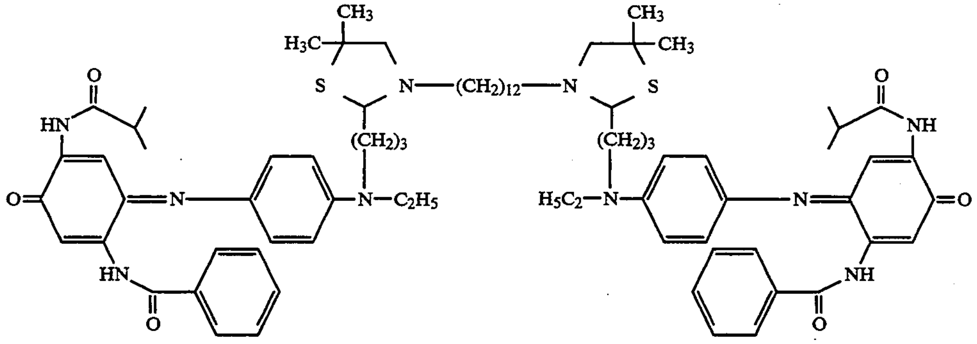

(xii)

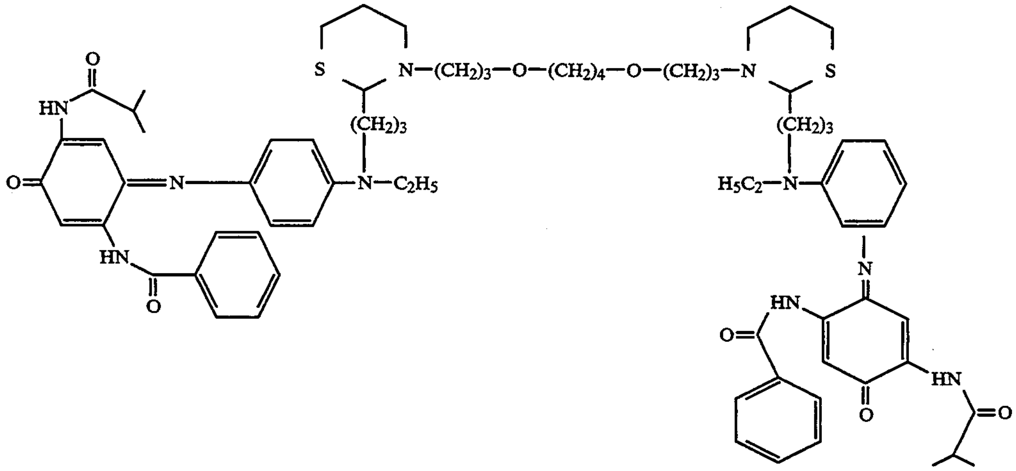

The color-providing compounds of the present invention may be synthesized by condensing a dye-substituted aldehyde, i.e., DYE-CHO with the salt of a bis(aminoethanethiol), e.g.,

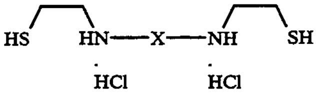

wherein X is a chemical linkage joining the two aminoethanethiol moieties. The bis(aminoethanethiol) compounds form the subject matter of the copending application of D. Messersmith and D. Waller, Ser. No. 923,859 filed on even date herewith. Rather than forming the cyclic 1,3-sulfur-nitrogen group as the final step in the synthesis, two equivalents of an intermediate possessing an aldehyde group may be condensed with the selected bis(aminoethanethiol) and the condensation product then reacted with the appropriate molecule or molecules to yield the final dye product. It will be appreciated that a dye-substituted ketone may be substituted for the aldehyde, particularly where it is desired to prepare spiro derivatives.

The dye-substituted aldehydes and ketones used above may be prepared by oxidation of the corresponding alcohol. The alcohols may be synthesized by procedures well known in the art. For example, the azomethine dyes containing an aldehyde or ketone functionality may be prepared by oxidation of the corresponding alcohol which in turn can be made by an oxidative coupling reaction between the corresponding coupler and silver halide developer moiety. The coupler and developer moieties are generally commercially available. If not, they can be prepared by procedures well known to one skilled in the art.

Alternatively, the color-providing compounds may be prepared by reacting two equivalents of a dye substituted with a cyclic 1,3-sulfur nitrogen group containing a reactive moiety on the nitrogen atom of the cyclic 1,3-sulfur-nitrogen group, i.e.,

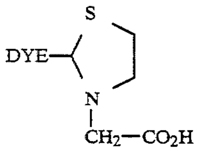

with a divalent organic radical, e.g., $H_2N-(CH_2)_3-NH_2$, to give the color-providing compound, i.e.,

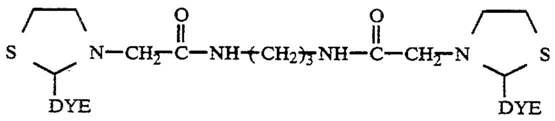

The dyes substituted with a cyclic 1,3-sulfur-nitrogen group may be prepared by the methods described in the aforementioned U.S. Pat. No. 4,098,783.

Still other procedures for preparing the subject compounds and further variations of those given above will be apparent to those skilled in the art.

The following detailed examples are given to illustrate the preparation of compounds within the scope of this invention, and are not intended to be in any way limiting.

EXAMPLE 1

Preparation of the compound of Formula (i).

To a slurry of 16.7 g of the bis(aminoethanethiol hydrochloride salt) having the structure

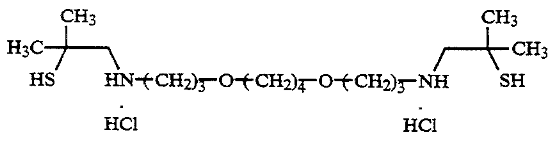

in 250 mL ethanol was added 7.4 g triethylamine. After stirring for several minutes, 30 g of the dye aldehyde having the structure

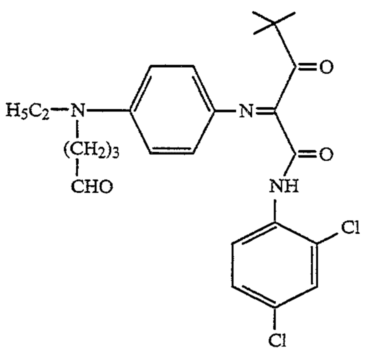

was added. A thick precipitate formed which was redissolved by the addition of 50 mL tetrahydrofuran. The reaction mixture was stirred at room temperature for about 65 hours. The ethanol was distilled off and 100 mL methylene chloride ($CH_2Cl_2$) was added. The $CH_2Cl_2$ layer was separated, dried over anhydrous sodium sulfate, and the $CH_2Cl_2$ removed under reduced pressure. The resulting residue was purified by column chromatography ($SiO_2$) using 2% methanol/$CH_2Cl_2$ as the eluent to yield 11.4 g of the title compound having the structure as shown in Formula (i). The structure was confirmed by mass spectroscopy.

The bis(aminoethanethiol salt) was made according to the procedure described in the aforementioned copending U.S. patent application, Ser. No. 923,859.

The dye aldehyde used above was prepared as follows:

To a stirred solution of 1.4 g oxalyl chloride in 30 ml $CH_2Cl_2$, cooled to −70° C. under $N_2$ was added dropwise a solution of 1.72 g dry dimethylsulfoxide (DMSO) in 10 ml $CH_2Cl_2$ at about −70° C. over several minutes. The resulting mixture was stirred at about −70° C. for 2–3 minutes followed by the dropwise addition of 4.9 g of the alcohol having the structure

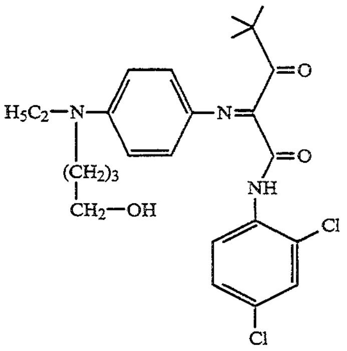

in 25 mL $CH_2Cl_2$ at about −70° C. over a period of about 10 minutes. The resulting mixture was allowed to stir at −70° C. for an additional 15 minutes followed by the portionwise addition of 5.1 g of triethylamine. After stirring at −70° C. for 5 minutes, the reaction mixture was warmed to 15° C. Water was added and the layers were separated. The $CH_2Cl_2$ layer was washed with brine, dried over anhydrous sodium sulfate, filtered and concentrated to yield a glassy residue. The residue was purified by column chromatography using silica gel with $CH_2Cl_2$ as eluent. The resulting gummy residue was triturated with petroleum ether to yield 3.41 g of the desired aldehyde. $^1$HNMR and mass spectroscopy confirmed the structure.

The alcohol used above was prepared by the oxidative coupling of

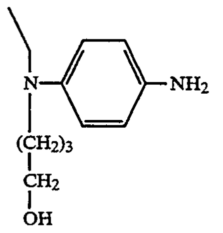
with
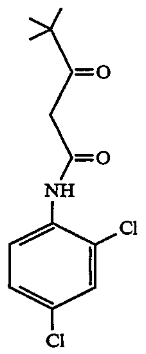

(both of which are commercially available) in the presence of potassium ferricyanide and potassium carbonate by a procedure well known in the art.

EXAMPLE 2

The compound of Formula (ii) was prepared in an analogous manner to that of the dye in Example 1 except that the bis(aminoethanethiol hydrochloride salt) condensed with the dye was

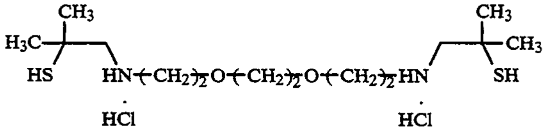

and sodium bicarbonate was used in place of the triethylamine. The structure was confirmed by $^1$HNMR and mass spectroscopy.

EXAMPLE 3

The compound of Formula (iii) was prepared in the same manner as that for the compound of Example 1 except that the dye condensed with the bis(aminoethanethiol hydrochloride salt) had the structure

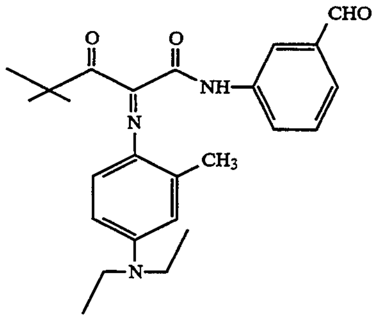

The dye aldehyde was prepared in a manner similar to that for the dye aldehyde in Example 1 starting with the corresponding alcohol. The structure of the final dye was confirmed by infrared and mass spectroscopy.

EXAMPLE 4

Preparation of the compound of Formula (iv).

(i) 3.4 g of the dye aldehyde, prepared as in Example 1, was combined with 2.0 g of the aminoethanethiol having the structure

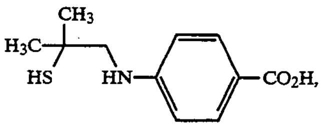

0.5 g of the sodium bicarbonate and 50 mL of benzene. The resulting mixture was refluxed using Dean-Stark trap to azeotrope the water. Several additions of benzene were made and the mixture was azeotroped until all the water was gone. The remaining benzene was removed in vacuo. $CH_2Cl_2$ was added and the mixture was washed with water and dilute hydrochloric acid. The $CH_2Cl_2$ layer was dried over anhydrous sodium sulfate, filtered and concentrated. The resulting residue was purified by column chromatography using silica gel with 5% methanol/$CH_2Cl_2$ as eluent to yield 780 mg of the thiazolidine dye having the structure

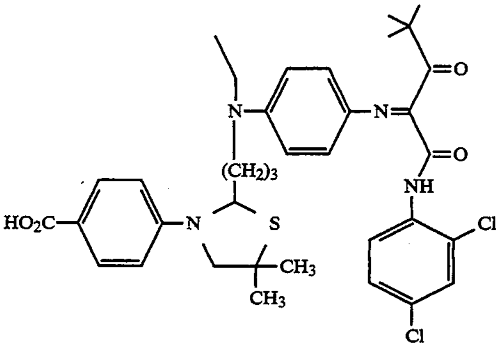

The structure was confirmed by NMR and mass spectroscopy.

The aminoethanethiol used above was prepared by combining 25.7 g of 6-aminohexanoic acid with 19.5 g of bis-isobutyraldehyde disulfide and 500 mL of toluene. The resulting mixture was refluxed several hours with a Dean-Stark trap to azeotrope the water. The toluene was removed in vacuo to yield an oil. The oil was taken up in 300 mL of methanol, and 18 g of sodium borohydride was added in small portions over a 1 hour period. The resulting mixture was stirred at room temperature overnight. 100 ml of 1N hydrochloric acid was added and the pH brought to 1 by the dropwise addition of concentrated hydrochloric acid. The methanol was removed in vacuo followed by the addition of 100 mL methanol which was again removed in vacuo to yield a yellow pasty residue. The residue was taken up in 250 mL of 95% ethanol and the resulting white precipitate was filtered. To the yellow filtrate was added zinc dust followed by concentrated hydrochloric acid. The zinc dust was filtered and the acid removed in vacuo to yield the desired aminoethanethiol. The structure was confirmed by NMR analysis.

(ii) 780 mg of the thiazolidine dye prepared in step (i), 496 mg tributylamine and 135 mg 1,4-bis(2-aminoethoxy)butane were dissolved in 10 mL of $CH_2Cl_2$. 414 mg of 2-iodo-1-methylpyridinium chloride was added and the reaction was refluxed under nitrogen for about 3.5 hours. The resulting mixture was cooled, washed with 0.5N hydrochloric acid and washed 3 times with water.

The reaction was concentrated to yield the title compound. $^{1}$HNMR, $^{13}$CNMR and mass spectroscopy confirmed the structure.

EXAMPLE 5

Preparation of the compound of Formula (vii). The compound was prepared according to the procedure of Example 2 except that the dye aldehyde condensed with the bis(aminoethanethiol hydrochloride salt) had the structure

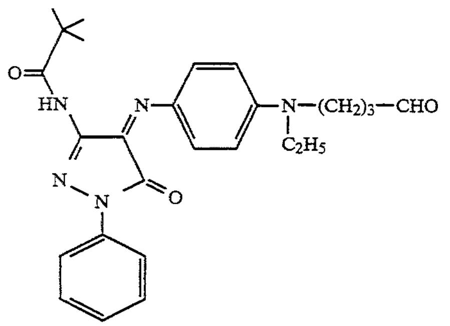

EXAMPLE 6

Preparation of the compound of Formula (viii). The compound was prepared according to the procedure of Example 1 except that the bis(aminoethanethiol hydrochloride salt) condensed with the dye aldehyde was

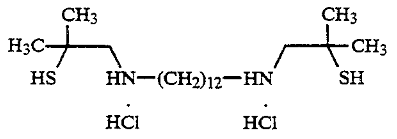

The structure of the title compound was confirmed by NMR and mass spectroscopy.

The bis(aminoethanethiol hydrochloride salt) was made according to the procedure described in the aforementioned copending U.S. patent application, Ser. No. 923,859.

EXAMPLE 7

Preparation of the compound of Formula (IX). The compound was prepared by a procedure analogous to that used in Example 4 except that the thiazolidine dye precursor used had the structure

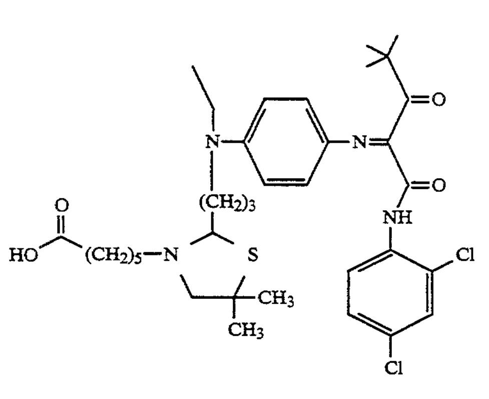

and 1,12-diaminododecane replaced the 1,4-bis(2-aminoethoxy)butane. The structure of the title compound was confirmed by $^{13}$CNMR, $^{1}$HNMR and mass spectroscopy.

As noted earlier, the color-providing materials according to the present invention are particularly useful for forming color images in heat-developable photosensitive image-recording systems. Specifically, the present invention provides a heat-developable color photosensitive image-recording material comprising (a) a support carrying in one or more layers a photosensitive silver halide, a reducing agent, a thermal solvent, a binder and a color-providing material capable of releasing a diffusible color-providing moiety upon cleavage in the presence of silver ions or a soluble silver complex, said color-providing material comprising two to four groups, the same or different, the groups being represented by the general formula

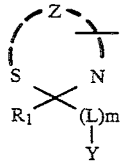

wherein Y represents a diffusible color-providing moiety; L represents a divalent organic linking group containing at least one carbon atom; m is 0 or 1; $R_1$ represents hydrogen, a monovalent organic radical or together with L represents the atoms necessary to complete a spiro union with the cyclic 1,3-sulfur-nitrogen group when m is 1 or together with Y represents the atoms necessary to complete a spiro union with the cyclic 1,3-sulfur-nitrogen group when m is 0; and Z represents the carbon atoms necessary to complete an unsubstituted or substituted 5- or 6-membered heterocyclic ring system provided each group represented by said formula is connected to the others by a multivalent chemical linkage which connects the groups through the N atom or through the C atoms represented by Z, and (b) on the same or a second support, an image receiving layer capable of receiving the diffusible color-providing moiety released from said color-providing material.

Preferably, the heat-developable color photosensitive image-recording material additionally contains a silver salt oxidizing material in a layer other than the image-receiving layer.

In addition, the heat-developable color photosensitive material also preferably includes an auxiliary ligand for silver. The use of auxiliary ligands in a heat-developable photosensitive material forms the subject matter of the copending U.S. patent application of J. Freedman, S. Sofen and K. Young, Ser. No. 923,859 filed on event date herewith.

As mentioned earlier, the color-providing materials of the present invention are substantially non-diffusible in the heat-developable photographic processing composition but capable of undergoing cleavage in the presence of the imagewise distribution of silver ions and/or soluble silver complex made available in the undeveloped and partially developed areas of the photosensitive emulsion as a function of development to liberate a more mobile and diffusible color-providing moiety in an imagewise distribution corresponding to the imagewise distribution of said ions and/or said complex.

The heat-developable color photosensitive image-recording materials using the compounds of this invention can be prepared in accordance with such procedures as disclosed in Research Disclosure No. 17029, issued June 1978.

The photosensitive silver halide used in the present invention may be any photosensitive silver halide employed in the photographic art, such as, silver chloride, iodide, bromide, iodobromide, chlorobromide, etc. and it may be prepared in situ or ex situ by any known method including using a light-sensitive silver halide forming component in the presence of the silver salt oxidizing material so as to form the light sensitive silver halide in part of the silver salt oxidizer.

The photosensitive silver halide emulsions used in the present invention may be spectrally sensitized by any known method in order to extend the photographic sensitivity to wavelengths other than those absorbed by the silver halide. Examples of suitable sensitizers include cyanine dyes, merocyanine, styryl dyes, hemicyanine dyes and oxonole dyes.

In addition to spectral sensitization, the silver halide emulsion may be chemically sensitized using any method known in the photographic art. However, it is preferred that there be no chemical sensitization.

The silver halide emulsion is generally added to each photosensitive layer in an amount calculated to give a coated coverage in the range of 0.5 to 8.0 mmol/m$^2$, preferably 0.5 to 4.0 mmol/m$^2$.

The silver salt oxidizing material should be relatively light stable and thermally stable under the processing conditions. The silver salt oxidizing material is generally an organic silver salt or silver salt complex as heretofore known in the art. Any organic compound known in the photographic art to be useful for forming the organic silver salt may be employed, see, e.g., those described in U.S. Pat. No. 4,729,942. See U.S. Pat. No. 4,260,677 for useful silver salt complexes.

Examples of suitable silver salt oxidizing materials include silver salts of carboxylic acids, e.g., behenic and stearic acids and silver salts of compounds having an imino group. Preferred silver salts are the organic silver salts having an imino group. The silver salts of benzotriazole and its derivatives have been found to give particularly good results in the heat-developable photosensitive systems of the present invention.

The silver salt oxidizer used in the present invention can be prepared in a suitable binder by any known means and then used immediately without being isolated. Alternatively, the silver salt oxidizer may be isolated and then dispersed in a suitable binder.

The silver salt oxidizer is generally used in an amount ranging from 0.5 to 8.0 mmol/m$^2$, and preferably from 0.5 to 4.0 mmol/m$^2$.

The reducing agents which may be used in the present invention may be selected from among those commonly used in heat-developable photographic materials. Illustrative reducing agents useful in the present invention include hydroquinone and its derivatives, e.g., 2-chlorohydroquinone; aminophenol derivatives, e.g., 4-aminophenol and 3,5-dibromophenol; catechol and its derivatives, e.g., 3-methoxycatechol; phenylenediamine derivatives, e.g., N,N-diethyl-p-phenylenediamine; and, 3-pyrazolidone derivatives, e.g., 1-phenyl-3-pyrazolidone and 4-hydroxymethyl-4-methyl-1-phenyl-3-pyrazolidone. The preferred reducing agents are 1-phenyl-3-pyrazolidone, commercially available under the tradename Phenidone, and 4-hydroxymethyl-4-methyl-1-phenyl-3-pyrazolidone, commercially available under the tradename Dimezone-S.

The reducing agents may be used singly or in combination and they are generally employed in amounts ranging from 0.5 to 8.0 mmol/m$^2$ and preferably 10 to 4.0 mmol/m$^2$.

Thermal solvents are compounds which are solids at ambient temperature but which melt at the temperature used for processing. The thermal solvent acts as a solvent for various components of the heat-developable photosensitive material, it helps to accelerate thermal development and it provides the medium for diffusion of various materials including silver ions and/or complexes, reducing agents and the dyes. Illustrative thermal solvents useful in the present invention include polar organic compounds such as the polyglycols described in U.S. Pat. No. 3,347,675 and the compounds described in U.S. Pat. No. 3,667,959. Particularly useful compounds include urea derivatives, e.g., dimethylurea, diethylurea and phenylurea; amide derivatives, e.g., acetamide, benzamide and p-toluamide; sulfonamide derivatives, e.g., benzenesulfonamide and α-toluenesulfonamide; and polyhydric alcohols, e.g., 1,2-cyclohexanediol and pentaerythritol. The thermal solvent designated TS-1 and having the structure

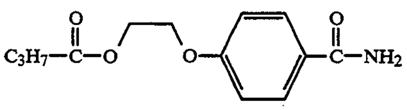

TS-1 has been found to give good results in the present invention.

The thermal solvent is generally incorporated on or in the image-receiving layer and/or in the photosensitive silver halide layer of the present invention. However, it may also be added to any intermediate layers and protective layers where necessary to obtain a desired result.

The thermal solvent is generally added in each layer in amounts ranging from 0.5 to 10.0 g/m$^2$, preferably 1.0 to 5.0 g/m$^2$.

The photosensitive silver halide emulsion layer(s) and other layers of the heat-developable photosensitive image-recording material may contain various materials as binders. Suitable binders include water soluble synthetic high-molecular weight compounds such as polyvinyl alcohol and polyvinylpyrrolidone and, synthetic or natural high-molecular weight compounds such as gelatin, gelatin derivatives, cellulose derivatives, proteins, starches and gum arabic. A single binder or mixture of binders may be used. Gelatin is the preferred binder for use in each layer.

The amount of binder used in each layer is generally 0.5 to 5.0 g/m$^2$, preferably 0.5 to 3.0 g/m$^2$.

The layers of the heat-developable photosensitive system according to the present invention which contain a crosslinkable colloid as a binder, e.g., gelatin, can be hardened by using various organic and inorganic hardeners such as those described in T. H. James, *The Theory of the Photographic Process,* 4th Ed., MacMillan, 1977, pp. 77-87. The hardeners can be used alone or in combination. It is preferred that the image-recording material according to the present invention contains a hardener in the photosensitive silver halide emulsion layer. Any suitable hardener known in the photographic art may be used, however, aldehyde hardeners, e.g. succinaldehyde and glyoxal, have been found to be particularly useful when gelatin is employed as the binder.

The hardeners are generally used in amounts ranging from 1 to 10% by weight of the total amount of gelatin coated.

The color-providing material may be added in the same layer as the photosensitive silver halide/silver salt oxidizer emulsion layer or in a layer on either side of the photosensitive emulsion layer. However, it is generally preferred that the color-providing material be placed so that exposure does not occur through the dye. If exposure is made through the dye, the dye may absorb the light needed to expose the silver halide. In certain instances, it may be desirable to separate the color-providing material from the emulsion layer by a spacer layer. Where the particular color-providing material chosen tends to be migratory during storage and/or thermal development of the heat-developable photosensitive system, it is preferred that the color-providing material be in a separate layer and more preferably, that it be in a layer furthest from the image-receiving layer.

The amount of color-providing material used varies with the type chosen but generally an amount of 0.25 to 2.0 mmol/$m^2$ is used.

The color-providing materials may be incorporated into the photographic layer(s) of the heat-developable photosensitive system by any suitable method. For example, the color-providing materials can be dissolved in a low boiling and/or high boiling solvent and dispersed in the binder, they can be dispersed in aqueous solutions of suitable polymers, e.g., gelatin, by means of a ball mill, or they can be solvent coated using any organic solvent that will also dissolve gelatin, e.g., trifluoroethanol or dimethylsulfoxide (DMSO).

Auxiliary ligands for silver which can be used in the present invention include 2,2'-bipyrimidine; 1,2,4-triazole and derivatives thereof, e.g., 3-phenyl-5-thienyl-1,2,4-triazole; phosphines, e.g., triphenylphosphine; acyclic thioureas, e.g., N,N'-di-n-butylthiourea and tetramethylthiourea; 3,6-dithia-1,8-octanediol; 6-substituted purines wherein the 6-position is substituted with —OR or —NHR' where R is hydrogen, alkyl, or aryl and R' is alkyl, e.g., 6-methoxypurine and 6-dodecylaminopurine; and, bidentate nitrogenous ligands having two nitrogen atoms which are both available to coordinate to the same silver atom, e.g., 4-azabenzimidazole and derivatives thereof, 2,2'-dipyridyls including 2,2'-dipyridyl, 4,4'-dimethyl-2,2'-dipyridyl and 4,4'-diphenyl-2,2'-dipyridyl and 1,10-phenanthrolines including 1,10-phenanthroline, 5-chloro-1,10-phenanthroline and 5-nitro-1,10-phenanthroline.

The auxiliary ligand may be present in any layer of the heat-developable photosensitive system of the present invention including the image-receiving layer. It may also be present on the image-receiving layer, in which case the layer also preferably contains a thermal solvent in which the ligand is soluble and a binder. Alternatively, water soluble ligands may be coated on the negative, i.e. on the layer comprising the photosensitive silver halide, before or after hardening of the gel has been accomplished. If the silver assisted cleavage of the particular color-providing material tends to be slow, it is preferred that the auxiliary ligand be present in a layer other than the image-receiving layer.

The auxiliary ligands are generally used in amounts which yield, after drying, a coating coverage of 1 to 36 mmol/$m^2$, preferably 2 to 24 mmol/$m^2$.

The support for the image-recording elements according to the present invention must necessarily be able to withstand the heat required for processing the image, and any suitable support can be employed such as those described in Research Disclosure No. 17029, issued June 1978. Specific examples of suitable supports include synthetic plastic films, such as a polyester film, a polyvinyl chloride film or a polyimide film and paper supports, such as, photographic raw paper, printing paper, baryta paper and resin-coated paper. Preferably, a polyester film is used.

A subcoat may be added to the face of the support which carries the heat-developable photosensitive materials in order to increase adhesion. For example, a polyester base coated with a gelatin subcoat has been found to enhance adhesion of aqueous based layers.

The heat-developable photosensitive image-recording material according to the present invention can be used to form monochrome or multicolor images. If the image-recording material is to be used to generate a full color-image, it generally has three different heat-developable light-sensitive layers each releasing a different color dye as a result of thermal development.

The heat-developable photosensitive diffusion transfer materials of the present invention include those wherein the photosensitive silver halide emulsion layer(s) and the image-receiving layer are initially contained in separate elements which are brought into superposition subsequent or prior to exposure. After development the two layers may be retained together in a single element, i.e., an integral negative-positive film unit or they can be peeled apart from one another. Alternatively, rather than being in separate elements, the photosensitive layer(s) and the image-receiving layer may initially be in a single element wherein the negative and positive components are contained in a heat-developable photosensitive laminate or otherwise retained together in an integral structure. After heat-development, the two layers may be retained together as a single element or they can be peeled apart from one another. Where the photosensitive silver halide emulsion layer(s) and the image-receiving layer are retained together as an integral negative-positive film unit, a masking layer, e.g., titanium dioxide, is necessary to conceal the untransferred dye from the final image.

The photosensitive material of the present invention may be exposed by any of the methods used in the photographic art, e.g., a tungsten lamp, a mercury vapor lamp, a halogen lamp, fluorescent light, a xenon flash lamp or a light emitting diode including those which emit infrared radiation.

The photosensitive material of the present invention is heat-developed after imagewise exposure. This is generally accomplished by heating the material at a temperature in the range of 80° to 200° C., preferably in the range of 100° to 150° C., for a period of from 1 to 720 seconds, preferably 1.5 to 360 seconds. In order to transfer the released dye to the image-receiving sheet, both heat and pressure must be applied simultaneously. Thus, pressure can be applied simultaneously with the heat required for thermal development by using heated rollers or heated plates. Alternatively, heat and pressure can be applied subsequent to thermal development in order to transfer the released dye.

All methods of heating that can be employed in heat-developable photosensitive systems known in the art may be applied to the heat-developable photographic material of the present invention. Thus, for example, heating may be accomplished by using a hot plate, an iron, heated rollers or a hot drum.

Any image-receiving layer which has the capability of receiving the dye released as a result of thermal development may be used in the present invention. Typical image-receiving layers which can be used are prepared by coating a support material with a suitable polymer for receiving the dye. Alternatively, certain polymers may be used as both the support and the dye receiving material.

The image-receiving layer is generally superposed on the photosensitive negative after exposure and the two are then heated simultaneously to develop the image and cause the dye to transfer. Alternatively, the negative may be exposed and then processed with heat, followed by superposing the image-receiving sheet on the exposed and developed photosensitive material and applying heat and pressure to transfer the dye. The image-receiving layer is then generally peeled apart from the negative.

Suitable polymers to be coated on the image-receiving support to receive dye include polyvinyl chloride, poly(methyl methacrylate), polyester, and polycarbonate.

The support materials which may be used for the image-receiving layer can be transparent or opaque. Examples of suitable supports are polymer films, such as, polyethylene terephthalate, polycarbonate, polystyrene, polyvinyl chloride, polyethylene, polypropylene and polyimide. The above supports can be made opaque by incorporating pigments therein, such as, titanium dioxide and calcium carbonate. Other supports include baryta paper, resin coated paper having paper laminated with pigmented thermoplastic resins, fabrics, glass, and metals.

Resin coated paper has been found to be a particularly useful support material for the image-receiving layer according to the present invention.

Additionally, the heat-developable photosensitive image-recording material of the present invention may include other materials heretofore suggested in the art but are not essential. These include, but are not limited to, antifoggants, antistatic materials, coating aids e.g, surfactants, activators and the like.

Also, the photosensitive elements may contain additional layers commonly used in the art, such as spacer layers, a layer of an antihalation dye, and/or a layer of a filter dye arranged between differentially color-sensitive emulsion layers. A protective layer may also be present in the image-recording material of the present invention. The protective layer may contain a variety of additives commonly employed in the photographic art. Suitable additives include matting agents, colloidal silica, slip agents, organofluoro compounds, UV absorbers, accelerators, antioxidants, etc.

The present invention is illustrated by the following photographic experiments.

In the following Examples, the silver iodobromide dispersion is a 0.25 μm cubic unsensitized iodobromide (2% iodide) emulsion prepared by standard techniques known in the art. The silver salt oxidizer, thermal solvent, dye-providing material and reducing agents used in the Examples were added to the coating compositions as dispersions. The various dispersions were prepared by the specific procedures described below or by analogous procedures but using different reagents as noted. The 1,2,4-triazole, glyoxal and succinaldehyde when added were added to the coating compositions as aqueous solutions.

(1) Silver Salt Dispersion 415 g of benzotriazole was added to 325 mL of concentrated ammonium hydroxide. To the resulting solution was added 450 g of gelatin and the mixture was diluted to a total volume of 6 liters with water. To this mixture, in the dark and at 40° C., was added a mixture prepared by combining 550 g of silver nitrate with 500 mL of concentrated ammonium hydroxide and diluted to a total volume of 2.1 liters with water. After the addition was complete, the material was washed using standard emulsion washing procedures and the pH adjusted to 6 and the pAg adjusted to 7.4.

(2) Thermal Solvent Dispersion 64 g of the thermal solvent designated TS-1, above, was dispersed in a mixture of 8.8 g of 10% aqueous polyvinyl- pyrrolidone, 10.8 g of 5% aqueous Alkanol XC (available from DuPont, Wilmington, Del.), and 160.4 g of water. The resulting mixture was ground in a ball mill for 7 hours. 100 g of water was introduced for washing purposes during the isolation of the dispersion.

(3) Dispersion of Dye-Providing Material 1.6 g of the dye-providing material of Formula (i) was dissolved in 5.0 g of ethyl acetate. 0.8 g of tricresylphosphate was added and the mixture was stirred and heated to 42° C. To the mixture at 42° C. was added a solution containing 21 g water, 4 g of 5% aqueous Alkanol XC and 8.5 g of 17.5% aqueous gelatin. The mixture was sonified with an ultrasonic probe for one minute in order to form a dispersion. The dispersion was stirred at 60° C. for 20 minutes to remove the ethyl acetate, followed by the addition of 14.1 g water.

(4) Reducing Agent Dispersion 3.0 g of reducing agent having the structure

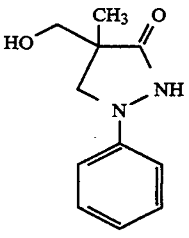

Dimezone S was added to 4.0 g of water and 3.0 g of 5% aqueous Alkanol XC. The resulting mixture was ground in a ball mill for 16 hours. The dispersion was diluted with water during isolation.

EXAMPLE 8

A heat-developable photosensitive material was prepared using the dispersions described above. A gelatin subcoated 4 mil polyester film (available from DuPont) was coated using a #30 Meyer Rod with an aqueous composition prepared in order to yield dry coating coverages of the respective components of layer 1 as follows:

| Layer 1 | |
|---|---|
| Gelatin (Inert, deionized, derivatized bone gelatin, available from Rousselot, France) | 3000 $mg/m^2$ |
| Dye-providing material | 0.25 $mmol/m^2$ |

-continued

| Layer 1 |
| --- |
| (Compound of Formula (i)) |

After air drying, layer 1 was overcoated with a composition (applied with a #30 Meyer Rod) prepared in order to yield coated coverages of the respective components of layer 2 as follows:

| Layer 2 | |
| --- | --- |
| Gelatin | 3000 mg/$m^2$ |
| Thermal Solvent (TS-1) | 1500 mg/$m^2$ |
| Reducing Agent (Dimezone S) | 4.0 mmol/$m^2$ |
| Silver Benzotriazole | 2.0 mmol/$m^2$ |
| Silver Iodobromide | 2.0 mmol/$m^2$ |
| Glyoxal | 100 mg/$m^2$ |
| 1,2,4-Triazole | 24.0 mmol/$m^2$ |

The heat-developable photosensitive material was exposed to white light for $10^{-3}$ sec. An image-receiving sheet comprising a resin coated paper base overcoated with polyvinylchloride (12 g/$m^2$) was superposed on the exposed, heat-developable photosensitive material and the assembly was processed at 110° C. for 180 sec at a pressure of 35 psi using a heated plate.

The photosensitive layer and dye-providing layer were peeled apart from the image-receiving layer after cooling below the melting point of the thermal solvent (104° C.), approximately 5 sec after processing. The maximum reflection density (Dmax) and the minimum density (Dmin) of the resulting image were measured using a reflection densitometer (MacBeth, model RD 514). The measured values are reported in Table 1.

TABLE 1

| | Dmax | Dmin |
| --- | --- | --- |
| EXAMPLE 8 | 0.89 | 0.68 |

EXAMPLE 9

Example 8 was repeated except that the dye-providing material of Formula (viii) was used in place of the dye-providing material of Formula (i).

The measured Dmax and Dmin values are reported in Table 2.

TABLE 2

| | Dmax | Dmin |
| --- | --- | --- |
| EXAMPLE 9 | 0.79 | 0.56 |

Examples 8 and 9 demonstrate that the dye-providing materials according to the present invention are useful in providing color images in a heat-developable photographic imaging system.

EXAMPLE 10

Three heat-developable imaging materials were prepared in a manner similar to Example 8 except that the photosensitive silver iodobromide, the silver benzotriazole and the reducing agent were left out and the dye-providing material was different in each. The coated coverages of the respective components of layer 1 and layer 2 were as follows:

| Layer 1 | |
| --- | --- |

-continued

| | |
| --- | --- |
| Gelatin | 2000 mg/$m^2$ |
| Dye-providing material | 0.50 mmol/$m^2$ |
| Layer 2 | |
| Gelatin | 3000 mg/$m^2$ |
| Thermal Solvent (TS-1) | 3000 mg/$m^2$ |
| Succinaldehyde | 100 mg/$m^2$ |

The three dye-providing materials used were the compound of Formula (i) and Compounds A and B shown below.

Compound A

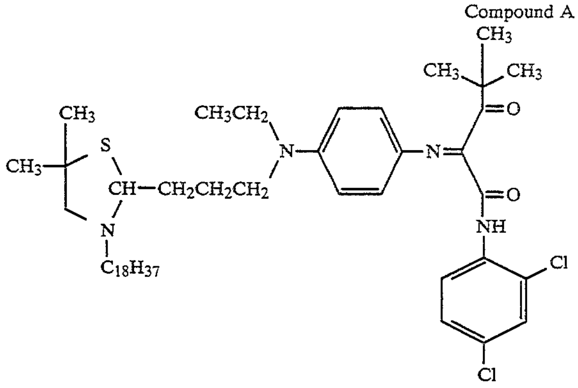

Compound B

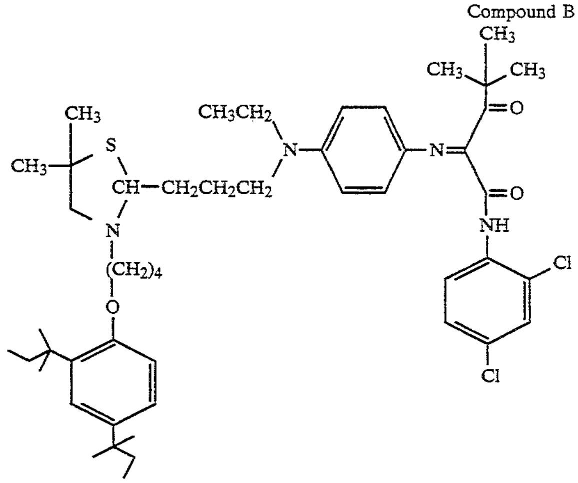

An image-receiving sheet comprising a resin coated paper base overcoated with polyvinylchloride (12 g/$m^2$) was superposed on each of the heat-developable materials and the resulting assemblies were processed by heating at 120° C. for 180 sec. at 35 psi using a heated plate. The dye-providing layer was peeled apart from the image-receiving layer after cooling below the melting point of the thermal solvent (110° C.), approximately 5 sec after processing. The optical reflection density for each was measured and the values are reported in Table 3.

TABLE 3

| | Density |
| --- | --- |
| EXAMPLE 10: | |
| Compound of Formula (i) | 0.19 |
| Compound A | 0.29 |
| Compound B | 0.45 |

The above data demonstrates that less uncleaved dye-providing material migrates when a dye-providing material according to the present invention is employed in a heat-developable imaging material compared to dye-providing materials having only one cyclic 1,3-sulfur-nitrogen moiety and one dye radical.

The heat-developable photosensitive materials prepared and processed in Examples 8, 9 and 10 above were processed base-free, i.e., they did not contain any added base or base-precursor and they were processed water-free, i.e., no water was added to aid in development or transfer. It is recognized what while certain of the auxiliary ligands used in the Examples may be classified as weak bases, such ligands would not be considered to be bases or base-precursors as those terms are used in Japanese Kokai No. 59-18054-8. However, as stated earlier, the color-providing compounds of the present invention may also be used in heat-developable imaging materials containing a base or base-precursor such as disclosed in the aforementioned Japanese Kokai No. 59-180548.

Since certain changes may be made in the above subject matter without departing from the spirit and scope of the invention herein involved, it is intended that all matter contained in the above description and the accompanying examples be interpreted as illustrative and not in any limiting sense.

We claim:

1. A compound represented by the formula

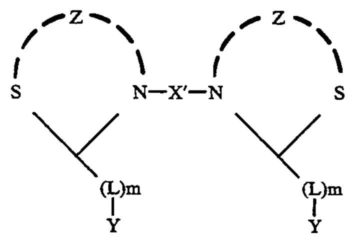

wherein Y represents a diffusible color-providing moiety; L represents a divalent organic linking group containing at least one carbon atom; m is 0 or 1; X′ represents a bivalent organic group joining the cyclic 1,3-sulfur-nitrogen groups; and Z represents the atoms necessary to complete a 5- or 6-membered heterocyclic ring system.

2. A compound represented by the formula

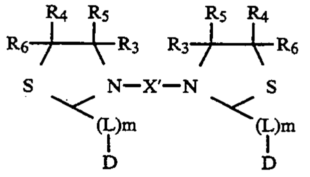

wherein L represents a divalent organic linking group containing at least one carbon atom; m is 0 or 1; X′ represents a bivalent organic group; $R_3$, $R_4$, $R_5$ and $R_6$ are each hydrogen, methyl or taken together, $R_3$ and $R_4$ or $R_5$ and $R_6$ represent a substituted or unsubstituted carbocyclic or heterocyclic ring, and D represents a complete dye selected from the group: nitro, thiazole, cyanine, di- and triphenylmethane, anthrapyridone, azo, anthraquinone, phthalocyanine, and azomethine.

3. A compound according to claim 2 wherein m is 1 and X′ is represented by —R—O—R′—O—R—, wherein R and R′ the same or different, represent alkylene.

4. A compound according to claim 2 wherein m is 1 and X′ is represented by —R—, wherein R represents alkylene.

5. A compound according to claim 2 wherein D is

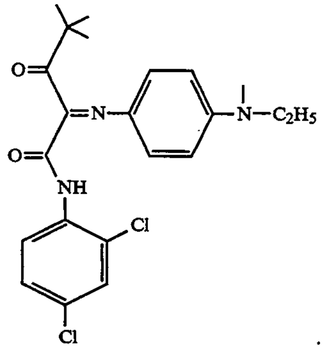

6. A compound represented by the formula

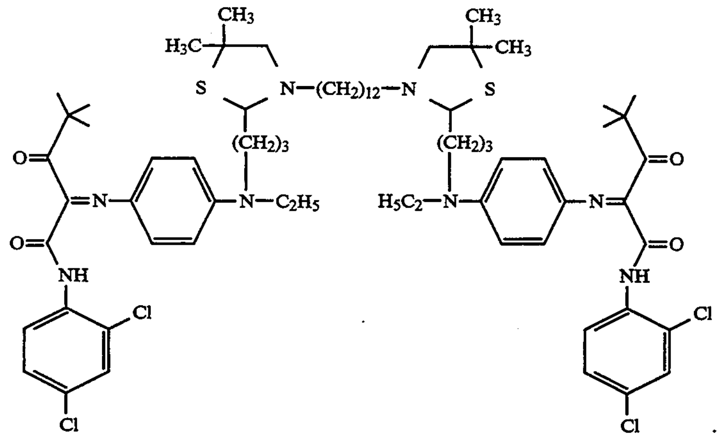

7. A compound according to claim 2 wherein X′ is selected from:

(a shared pair of electrons);

R;

R—O—R—;

R—O—R′—;

R—O—R′—O—R—;

R—O—R′—O—R″—;

Ar—CO—NH—R—O—R′—O—R—NH—CO—Ar—;

R—CONH—R′—NH—CO—R—;

R—NH—$SO_2$—R—$SO_2$—NH—R—;

R—NH—$SO_2$—R′—$SO_2$—NH—R—;

R—NH—$SO_2$—R′—$SO_2$—NH—R″—;

NH—R—NH—R—NH—;

NH—R—NH—R′—NH—;

NH—R—NH—R—NH—R—NH—;

NH—R—NH—R′—NH—R—NH—;

NH—R—NH—R′—NH—R″—NH—, wherein R, R′, and R″ are bivalent hydrocarbon residue and Ar is aryl.

* * * * *